United States Patent
Dioguardi

(10) Patent No.: US 9,615,575 B2
(45) Date of Patent: Apr. 11, 2017

(54) COMPOSITION FOR ELIMINATION OF TROUBLESOME VARMINTS

(71) Applicant: DETERMINANTS OF METABOLISM RESEARCH LABORATORY S.r.l., Castel San Giovanni (PC) (IT)

(72) Inventor: Francesco Saverio Dioguardi, Milan (IT)

(73) Assignee: Determinants of Metabolism Research Laboratory S.r.l., Castel San Giovanni (PC) (IT)

( * ) Notice: Subject to any disclaimer, the term of this patent is extended or adjusted under 35 U.S.C. 154(b) by 0 days.

(21) Appl. No.: 14/189,543

(22) Filed: Feb. 25, 2014

(65) Prior Publication Data

US 2014/0371289 A1 Dec. 18, 2014

(51) Int. Cl.
*A61K 31/4985* (2006.01)
*A01N 37/44* (2006.01)
*A01N 25/00* (2006.01)

(52) U.S. Cl.
CPC ........... *A01N 37/44* (2013.01); *A01N 25/004* (2013.01)

(58) Field of Classification Search
None
See application file for complete search history.

(56) References Cited

U.S. PATENT DOCUMENTS 5,658,895 A * 8/1997 Aoi et al. .......... 514/58

FOREIGN PATENT DOCUMENTS

| AU | 14733 99 | 8/1999 |
| EP | 0 481 791 | 4/1992 |
| WO | WO 2010/036767 | 4/2010 |
| WO | WO 2010/127069 | 11/2010 |

OTHER PUBLICATIONS

X. Li et al., "Composition of Amino Acids in Feed Ingredients for Animal Diets", Amino Acids, vol. 40, No. 4, Sep. 15, 2010, pp. 1159-1168.
Database WPI, Week 198303, Thomson Scientific, XP-002716490, 2 pages.
Search Report for IT TO201301493 dated Nov. 18, 2013.

* cited by examiner

*Primary Examiner* — San-Ming Hui
*Assistant Examiner* — Andrew Lee
(74) *Attorney, Agent, or Firm* — Nixon & Vanderhye P.C.

(57) ABSTRACT

Composition for elimination of troublesome varmints comprises all the non-essential amino acids alanine, glycine, proline, serine, tyrosine, aspartic acid, asparagine, glutamic acid.

13 Claims, No Drawings

COMPOSITION FOR ELIMINATION OF TROUBLESOME VARMINTS

This claims priority to Italian Patent Application No. IT T02013A000493 filed 14 Jun. 2013, the entire contents of each of which are hereby incorporated by reference.

FIELD OF THE INVENTION

The present disclosure concerns a new composition for the elimination of troublesome varmints which is free of environment polluting effects.

BACKGROUND OF THE INVENTION

Rodentia, Lagomorpha and Columbiformes are some of the orders of varmint species infesting human environment and reduction of their number is often a problem due to their metabolic resistance to poisons.

Moreover, poisons dispersed in the environment are dangerous for many other animals and may also be harmful for humans.

OBJECT AND SUMMARY OF THE INVENTION

Object of the present invention is to provide a new biocide composition for the elimination of troublesome varmints which is free of environment polluting effects.

According to the invention, the above object is achieved thanks to the compositions specified in the ensuing claims, which are understood as forming an integral part of the present description.

In an embodiment, the present disclosure provides for an amino acid based biocide composition for the elimination of troublesome varmints, wherein the composition comprises all the non-essential amino acids (alanine, glycine, proline, serine, tyrosine, aspartic acid, asparagine, glutamic acid).

In another embodiment, the amino acid based biocide composition for the elimination of troublesome varmints herein disclosed further comprises arginine and glutamine.

In a further embodiment, the composition herein disclosed comprises glutamine and arginine in an amount up to 50% on a weight ratio with respect to all the non-essential amino acids.

DETAILED DESCRIPTION OF THE INVENTION

Varmint species of human environment can represent a severe danger for the public health.

Rodent-borne diseases, for example, can be transferred directly to humans through bite wounds or consumption of contaminated food and/or water, or indirectly by way of ticks, mites, and fleas that transmit the infection to humans after feeding on infected rodents.

The detailed description provides experimental data about the effects as biocide achieved by the amino acid composition herein disclosed on mice.

Nevertheless these data are not to be construed as a limitation of the uses of the present amino acid biocide composition, since it can be administered to several troublesome varmint species which can spread diseases, destroy crops or property, kill animals. Other troublesome varmint species can comprise, for example, rats, prairie dogs, squirrels, rabbits, hares, pikas, groundhogs, racoons, pigeons or starlings.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

While studying epigenetic modifications induced by different nitrogen content of calorically balanced diets in laboratory animals, isonitrogenous compositions of non-essential amino acids (NEAR) also enriched with arginine and glutamine (briefly named NEAA-CEAA) were tested.

Unexpectedly, such compositions determined death of all the laboratory animals in a few days.

The laboratory animals were fed with the herein disclosed composition (in an amount of 20% by weight with respect to the feed total weight) supplemented with carbohydrates and lipids as well as vitamins and mineral salts to address the nutritional requirements for rodents, and specifically for mouse, according to Nutrient Requirements of Laboratory Animals, $4^{th}$ revised edition, 1995, pages 80 to 102, available i.a. on internet, http//www.nap.edu/openbook.php?record_id=4758&page=80

As control, laboratory animals were fed with two different amino acid compositions, one containing only essential amino acids (EAA) plus tyrosine and cysteine in peculiar ratios to phenylalanine and methionine, respectively, and the other one replicating the casein ratios of NEAA to EA. Such a first composition (EAA) is disclosed i.a. in EP 1 670 453.

The different amino acid compositions were prepared in form of pellets.

The early death of rodents fed with the NEAR-CERA composition opens a new field of application of nutritional sciences: how to kill varmints without polluting environment and targeting - with abundance of food instead of poisoned food- reduction of rodents populations by adequate pellets. The most animals would eat, the most rapidly they will die. Small animals, weanling animals would be eliminated far before largest, oldest animals and the effects on pregnating animals may be also taken in account both for the deadly effects on females and on reducing the number of living newborns. Therefore, the composition herein disclosed can be used as biocide for eliminating troublesome varmints species of human environment.

According to the present disclosure, the non-essential amino acids (NEAA) included in the composition are alanine, glycine, proline, serine, tyrosine, aspartic acid, asparagine, glutamic acid. The composition envisages, as further active ingredients, glutamine and arginine. Glutamine and arginine are preferably present in an amount up to 50% on a weight ratio with respect to the non-essential amino acids.

The composition preferably comprises alanine and arginine in a weight ratio comprised between 2 and 3, more preferably equal to 2.5.

The weight ratio between alanine and the sum of arginine and glutamine can be comprised between 1 and 1.5, preferably equal to 1.35.

Preferably, the weight ratio between the sum of proline plus glutamine versus tyrosine is comprised between 18 and 30, preferably equal to 24.0

Glutamic acid and glutamine can be present in a weight ratio comprised between 4 and 8, preferably equal to 6.0.

The composition can comprises glycine and serine in a weight ratio comprised between 2 and 3, preferably equal to 2.5.

Proline and serine can be present in a weight ratio comprised between 1 and 3, preferably equal to 2.0.

Furthermore, still preferably:
the weight ratio between serine versus the sum of glutamic acid, asparagine, aspartic acid and tyrosine is comprised between 0.5 and 1.5, preferably equal to 1.0;
serine and tyrosine are present in a weight ratio comprised between 4.5 and 7.5, preferably equal to 6.0;
glutamic acid and asparagine are present in a weight ratio comprised between 0.5 and 1.5, preferably equal to 1.0;
asparagine and aspartic acid are present in a weight ratio comprised between 1 and 3, preferably equal to 2.0.

An example of formulation of the composition according to the present disclosure is given in the Table 1 reported hereinafter (specifically the composition named NEAA-CEAA).

Materials and Methods

The experimental protocol was approved and conducted in accordance with the Italian Ministry of Health and complied with the *The National Animal Protection Guidelines*.

Three groups of 75 animals, CD1 mice inbread "swiss type" males and females of the same age, were randomized after lactation and were assigned to the 3 different types of isocaloric, isonitrogenous diets differing only for nitrogen content.

Animals were caged in groups of 10 animals per cage, 5 males and 5 females, at standard light and temperature conditions, fed with water and pellet ad libitum.

Any 48 hours water and food consumption was recorded, and did not varied among cages and type of pellet for the first 2 days. Animals ate about 4.5 grams/day of any pellet (considering an average weight of a mouse of about 15-30 g, each mouse introduced an amount of pellet equal to about 0.15-0.30 g/body g per day).

The pellets compositions of the three tested diets are shown in table 1.

TABLE 1

| Amino acid | Diet 1 NEAA-CEAA (mg) | Diet 2 EAA (mg) | Diet 3 Casein-like (mg) |
|---|---|---|---|
| L-Leucine |  | 31.25 | 9.50 |
| L-Isoleucine |  | 15.62 | 6.00 |
| L-Valine |  | 15.62 | 6.50 |
| L-Lysine |  | 16.25 | 7.00 |
| L-Threonine |  | 8.75 | 4.00 |
| L-Histidine |  | 3.75 | 2.80 |
| L-Phenylalanine |  | 2.50 | 5.00 |
| L-Methionine |  | 1.25 | 2.50 |
| L-Tryptophan |  | 0.50 | 1.30 |
| L-Tyrosine | 1.00 | 0.75 | 5.00 |
| L-Cystine |  | 3.75 |  |
| L-Cysteina |  |  | 0.80 |
| L-Alanine | 35.00 |  | 3.20 |
| L-Arginine | 14.00 |  | 3.40 |
| L-Glycine | 15.00 |  | 2.40 |

TABLE 1-continued

| Amino acid | Diet 1 NEAA-CEAA (mg) | Diet 2 EAA (mg) | Diet 3 Casein-like (mg) |
|---|---|---|---|
| L-Proline | 12.00 |  | 9.50 |
| L-Glutamine | 12.00 |  | 9.50 |
| L-Serine | 6.00 |  | 5.10 |
| L-Aspartic acid | 1.00 |  | 3.50 |
| L-Asparagine | 2.00 |  | 3.50 |
| L-Glutamic acid | 2.00 |  | 9.50 |
| Total composition (mg) | 100.00 | 100.00 | 100.00 |

Results

After 3 days animals fed with the NEAR-CERA composition (reported in table 1) started suddenly to die with noticeably behavioral differences between males and females.

More than 25% of all animals died between 72 and 96 hours from the beginning of observation and all the remaining animals died in 10 days.

Males were extremely active at the beginning and aggressive among them while females reduced markedly their movements.

The few males that lived more than 7 days survived for evident episodes of cannibalism, but died rapidly, in few hours (<36 h), when isolated.

In order to exclude the animal's young age and small weight as factors in their early death, healthy adult mice, previously fed with the casein-like and EAA diets were fed with the new isocaloric, isonitrogenous NEAA-CEAA diet.

Healthy 6 to 12 months mice were thus switched to NEAA-CEAA diet and they died—with behaviors perfectly overlapping with what observed in weanling mice—in a period comprised between 7 to 20 days.

Post-mortem examination of dead mice showed at least three relevant events in all animals: a monstrous dilative cardiomyopathy, 30 to 70% atrophy of kidneys mostly in the cortex but with extended damages also in the medullar part, atrophy and flattening of intestinal villi.

The animals fed with EAA and Casein-like pellet lived for more than 24 months and, quite peculiarly, mice fed with EAA only lived for more than 30 months.

Considering that the animals ate about 4.5 grams/day of pellets, that the tested biocide compositions were contained in an amount of 20% by weight of the pellets total weight and that CEAA are preferably present in an amount up to 50% by weight with respect to the NEAA, the amount of NEAA assumed by the animals (having a body weight about 15-30 g) which is sufficient to determine the lethal effects herein disclosed is about 0.59 g/day per animal (20-39 mg/body g per day).

Animals fed with pellets containing only NEAA without conditionally essential amino acids such as glutamine and arginine (CEAA) assumed an average amount of pellet equal to about 3.92±0.16 g/day (13% less pellet intake on a 48 hours observation period, 2 groups of 10 different male animals). These animals died in the same time period of the animals which assumed the NEAA-CEAA composition and the post-mortem examination showed dilative cardiomyopathy, kidney atrophy, and atrophy and flattening of intestinal villi.

The invention claimed is:
1. A biocide composition containing;
amino acids that only consist of:
alanine, glycine,
proline,
serine,
tyrosine,
aspartic acid,
asparagine,
glutamic acid,
glutamine, and
arginine,
wherein glycine and serine are present in a weight ratio between 2 and 3,
wherein proline and serine are present in a weight ratio between 1 and 3,
wherein a weight ratio of serine versus a sum of glutamic acid, asparagine, aspartic acid and tyrosine is between 0.5 and 1.5, and
wherein serine and tyrosine are present in a weight ratio between 4.5 and 7.5;
wherein the composition acts as a biocide to varmints.

2. The biocide composition according to claim 1, wherein alanine and arginine are present in a weight ratio between 2 and 3.

3. The biocide composition according to claim 1, wherein the weight ratio between alanine versus the sum of arginine and glutamine is between 1 and 1.5.

4. The biocide composition according to claim 1, wherein the weight ratio between the sum of proline plus glutamine versus tyrosine is between 18 and 30.

5. The biocide composition according to claim 1, wherein glutamic acid and glutamine are present in a weight ratio between 4 and 8.

6. The biocide composition according to claim 1, wherein glutamic acid and asparagine are present in a weight ratio between 0.5 and 1.5.

7. The biocide composition according to claim 1, wherein the troublesome varmint species are species belonging to the following orders:
Rodentia, Lagomorpha and Columbiformes.

8. Use of the biocide composition according to claim 1 for eliminating troublesome varmints species of human environment.

9. A biocide composition containing:
amino acids that only consist of:
alanine,
glycine,
proline,
serine,
tyrosine,
aspartic acid,
asparagine, and
glutamic acid,
wherein glycine and serine are present in a weight ratio between 2 and 3,
wherein proline and serine are present in a weight ratio between 1 and 3,
wherein a weight ratio of serine versus a sum of glutamic acid, asparagine, aspartic acid and tyrosine is between 0.5 and 1.5, and
wherein serine and tyrosine are present in a weight ratio between 4.5 and 7.5;
wherein the composition acts as a biocide to varmints.

10. The biocide composition according to claim 9, wherein glutamic acid and asparagine are present in a weight ratio between 0.5 and 1.5.

11. The biocide composition according to claim 9, wherein asparagine and aspartic acid are present in a weight ratio comprised between 1 and 3.

12. The biocide composition according to claim 9, wherein the troublesome varmint species are species belonging to the following orders:
Rodentia, Lagomorpha and Columbiformes.

13. Use of the biocide composition according to claim 9 for eliminating troublesome varmints species of human environment.

* * * * *